United States Patent [19]

Rao et al.

[11] Patent Number: 5,717,061
[45] Date of Patent: Feb. 10, 1998

[54] SYNTHETIC ANTIMICOBIAL PEPTIDES

[75] Inventors: A. Gururaj Rao, Urbandale, Iowa; Lingxiu Zhong, Bozeman, Mont.

[73] Assignee: Pioneer Hi-Bred International, Inc., Des Moines, Iowa

[21] Appl. No.: 440,174

[22] Filed: May 12, 1995

Related U.S. Application Data

[60] Division of Ser. No. 179,632, Jan. 7, 1994, Pat. No. 5,607,914, which is a continuation-in-part of Ser. No. 79,512, Jun. 18, 1993, abandoned, which is a continuation-in-part of Ser. No. 3,884, Jan. 13, 1993, abandoned.

[51] Int. Cl.$^6$ .............. C07K 7/00; C07K 14/00; A61K 38/04; A61K 38/16
[52] U.S. Cl. .............. 530/300; 530/324; 530/326; 530/327; 514/2; 514/12
[58] Field of Search ............... 530/300, 324, 530/326, 327; 514/2, 12

Primary Examiner—Robert A. Wax
Assistant Examiner—Elizabeth Slobodyansky

[57] ABSTRACT

Synthetic polypeptides exhibiting amphipathic alpha-helices provide cell-expressible antimicrobial activity.

2 Claims, No Drawings

SYNTHETIC ANTIMICROBIAL PEPTIDES

CROSS REFERENCE TO PARENT APPLICATION

This is a divisional application of the prior application Ser. No. 08/179,632, filed Jan. 7, 1994, now U.S. Pat. No. 5,607,914, which is a continuation in part of application Ser. No. 08/079,512, filed Jun. 18, 1993, now abandoned, which was a continuation in part of application Ser. No. 08/003,884, filed Jan. 13, 1993, now abandoned.

TECHNICAL FIELD

This invention relates to synthetic peptides which have antimicrobial activity.

BACKGROUND OF THE INVENTION

Disease resistance is an important objective of the genetic engineering of crop plants. Numerous fungi and bacteria are serious pests of common agricultural crops. The maize plant is susceptible to a variety of pathogenic fungi that reduce yield and quality of the crop all over the world. In the United States alone annual losses in the Corn Belt range from about 7% to about 17%. One method of controlling diseases has been to apply antimicrobial organic or semiorganic chemicals to crops. This method has numerous, art-recognized problems. A more recent method of control of microorganism pests has been the use of biological control organisms which are typically natural competitors or inhibitors of the troublesome microorganisms. However, it is difficult to apply biological control organisms to large areas, and even more difficult to cause those living organisms to remain in the treated area for an extended period. Still more recently, techniques in recombinant DNA have provided the opportunity to insert into plant cells cloned genes which express antimicrobial compounds. This technology has given rise to additional concerns about eventual microbial resistance to well-known, naturally occurring antimicrobials, particularly in the face of heavy selection pressure, which may occur in some areas. Thus, a continuing effort is underway to express naturally occurring antimicrobial compounds in plant cells directly by translation of a single structural gene.

However, there is a limited pool of naturally occurring peptides and other compounds with which molecular biologists can work. Attention is now focused on the rational design of entirely new peptides which can function effectively in plant cell expression systems and in other uses where antimicrobial peptides can be used.

In addition, there are other aspects of plant cell expression systems which make the design of new antimicrobial peptides desirable. Crop plants have more important things to do than fight disease. They are sources of sugars, starches, proteins, oils, fibers, and other raw materials. Genetic engineers would also like to modify, and often to enhance, the production of those natural plant products. Unfortunately, plant cells can only produce large quantities of a few cellular components at a time. If they are producing high levels of storage proteins, it is difficult for them to also produce high levels of antifungal compounds. Thus, genetic engineers face a quandary in designing advanced plant systems which require high-level expression of multiple genes. The creation of entirely new antimicrobial peptides offers the molecular designer the opportunity to select structures which enhance the plant's content of various important or limiting amino acids while also providing antimicrobial activity. One example of this is the copending application of Rao and Beach, "High Lysine Derivatives of Alpha-Hordothionin", Ser. No. 08/003,885, filed Jan. 13, 1993. Even so, there continues to exist a need for still more compounds which can be evaluated and used in various plant and non-plant antimicrobial applications.

The principle of amphipathy has been used in the past to design biologically active proteins. In 1981 De Grado et al., *J.Am.Chem.Soc.* 103:679–681 showed that the completely synthetic analog of melittin was biologically active even though it had no homology to the natural peptide. Fink et al., *Int.J.Pep.Prot.Res.* 33:412–421 (1989) and Boman et al. *FEBS Lett.* 1:103–106 (1989) have demonstrated antibacterial activity of synthetic cecropin-like model peptides and cecropin-melittin hybrid compounds. Lee et al., *Biochem.Biophys.Acta* 862:211–219 (1986) and Agawa et al., *J.Biol.Chem.* 266:20218–20222 (1991) have shown a relationship between antimicrobial activity and amphiphilic properties of basic model peptides. More recently, Moser, *Protein Eng.* 5:323–331 (1992) has reported on the design, synthesis and structure of an amphipathic peptide with pH-inducible hemolytic activity. Taylor et al., *Molec.Pharm.* 22:657–666 (1982) have synthesized analogs of beta-endorphin possessing complete biological activity. Frohlich and Wells, *Int.J.Pep.Prot.Res.* 37:2–6 (1991) have suggested the idea of peptide amphipathy in the design of mechanism-based insecticides.

DISCLOSURE OF THE INVENTION

It has now been determined that new lytic peptides can be designed to provide antifungal or antimicrobial activity. These proteins can be expressed to enhance resistance to fungal diseases in plants. While not intending to be limited by theory, this discovery is based upon a departure from prior art methods involving de novo synthesis of compounds. Instead, the compounds of this invention were designed according to the principle that, so long as the amphipathic helix secondary structure constitutes the predominant portion of the molecule (i.e., that which determines its physico-chemical behavior), the peptide sequence can be constructed with as much or as little sequence homology as desired to existing bioactive compounds, or with no sequence homology at all to existing bioactive compounds, provided that it has a hydrophobic moment as determined by the Eisenberg algorithm (Eisenberg et al., *J.Mol.Biol.* 179:125–142, 1984) which is similar to that of naturally occurring bioactive molecules. In general, this hydrophobic moment can be expected to place them in the SURFACE region of the hydrophobic moment plot of naturally occurring antimicrobial proteins as defined by Eisenberg and colleagues.

The compounds of this invention have amino acid sequences as indicated in SEQUENCE I.D. Nos. 1 through 22. Although them is little or no sequence homology in these peptides at the primary structure level, there is considerable similarity at the secondary structure and hydrophobic moment levels, which structural similarity is responsible for their similar antimicrobial activities. These peptides are all characterized by a common structural theme that is critical to their lytic to activity, namely, regions which form amphipathic alpha helices. In such a helix the hydrophobic amino acid residues are oriented on one face of the helix and the hydrophilic amino acids are oriented on the other face. While not intending to be limited by theory, it appears that this is the structural element which is capable of interacting with and permeabilizing the plasma membranes of a broad spectrum of target organisms, including both bacteria and fungi, eventually leading to cell death.

Comparison of some of the sequences illustrates the principle that design of these synthetic compounds offers considerable flexibility in selection of amino acid and other profiles while retaining antimicrobial activity. SEQUENCE I.D. Nos. 3 and 4 are quite similar, yet several arginine residues in SEQUENCE I.D. No. 3 have been replaced by lysine residues in SEQUENCE I.D. No. 4. The same observation can be made by comparison of SEQUENCE I.D. No. 9 and SEQUENCE I.D. No. 10. Since lysine is a limiting amino acid in maize, this design flexibility offers the opportunity to impart disease resistance to maize with a high-lysine peptide if desired.

It has now also been determined that there is a much smaller, potentially minimum, functional fragment of several of these sequences, as identified in SEQUENCE I.D. No. 16. This sequence has good antimicrobial activity despite being several residues smaller than the other sequences shown. Since hydrophobic moment is the most important measure of antimicrobial potential, this invention also provides a peptide of 15 to 30 amino acids comprising the amino acid sequence of SEQUENCE I.D. No. 16, having a hydrophobicity (H) of −0.34 to −0.50 and a hydrophobic moment (μH) of from about 0.60 to about 0.84. An example of such a peptide is provided in SEQUENCE I.D. No. 17. Other, similar sequences are indicated in SEQUENCE I.D. Nos. 19–22. Yet another peptide meeting the requirements of hydrophobicity and hydrophobic moment is SEQUENCE I.D. No. 18, which has a hydrophobicity of −0.49 and a hydrophobic moment of 0.64.

Synthesis of the compounds described herein was performed according to methods of peptide synthesis which are well known in the art and thus constitute no part of this invention. In vitro, we have synthesized the compounds on an Applied Biosystems Model 431A peptide synthesizer using FastMoc™ chemistry involving HBtu [2-(1H-benzotriazol-1-yl)-1,1,3,3-tetramethyluronium hexafluorophosphate, as published by Rao et al., *Int. J. Pep. Prot. Res.* 40:508–515 (1992). Peptides were cleaved following standard protocols and purified by reverse phase chromatography using standard methods. The amino acid sequence of each peptide was confirmed by automated Edman degradation on an Applied Biosystems 477A protein sequencer/120A PTH analyzer. More preferably, however, the compounds of this invention are synthesized in vivo by bacterial or plant cells which have been transformed by insertion of an expression cassette containing a synthetic gene which when transcribed and translated yields the desired compound. Such empty expression cassettes, providing appropriate regulatory sequences for plant or bacterial expression of the desired sequence, are also well-known, and the nucleotide sequence for the synthetic gene, either RNA or DNA, can readily be derived from the amino acid sequence for the protein using standard reference texts. Preferably, such synthetic genes will employ plant-preferred codons to enhance expression of the desired protein.

INDUSTRIAL APPLICABILITY

The following description further exemplifies the compositions of this invention and the methods of making and using them. However, it will be understood that other methods, known by those of ordinary skill in the art to be equivalent, can also be employed.

Plants

The polypeptides employed in this invention can be effectively applied to plants afflicted with susceptible microorganisms by any convenient means, including spray, creams, dust or other formulation common to the antimicrobial arts. The compound can also be incorporated systemically into the tissues of a treated plant so that in the course of infesting the plant the pathogens will be exposed to antimicrobial amounts of the compound of this invention. One method of doing this is to incorporate the compound in a non-phytotoxic vehicle which is adapted for systemic administration to the susceptible plants. This method is commonly employed with fungicidal materials such as captan and is well within the purview of one of ordinary skill in the art of plant fungicide formulation. However, since the genes which code for these compounds can be inserted into an appropriate expression cassette and introduced into cells of a susceptible plant species, an especially preferred embodiment of this method involves inserting into the genome of the plant a DNA sequence coding for a compound of this invention in proper reading frame, together with transcription initiator and promoter sequences active in the plant. Transcription and translation of the DNA sequence under control of the regulatory sequences causes expression of the protein sequence at levels which provide an antimicrobial amount of of the protein in the tissues of the plant which are normally infected by the pathogens.

The plant is preferably a plant susceptible to infection and damage by one or more of *F. graminearum, Fusarium moniliforme, F. oxysporum, A. flavus, P. medicaginis, Alternaria longipes, Colletototrichum graminicola, Verticillium albo-atrum, Phytophthora megasperme* f. sp. *glycinea, Macrophomina phaseolina, Diasporthe phaseolorum caulivor, Sclerotinia sclerotiorum,* and *Sclerotinia trifoliorum.* These include corn (*Zea mays*) and sorghum (*Sorghum bicolor*). However, this is not to be construed as limiting, inasmuch as these two species are among the most difficult commercial crops to reliably transform and regenerate, and these pathogens also infect certain other crops. Thus the methods of this invention are readily applicable via conventional techniques to numerous plant species, if they are found to be susceptible to the plant pathogens listed hereinabove, including, without limitation, species from the genera Allium, Antirrhinum, Arabidopsis, Arachis, Asparagus, Atropa, Avena, Beta, Brassica, Browallia, Capsicum, Cicer, Cicla, Citrullus, Citrus, Cucumis, Cucurbita, Datura Daucus, Digitalis, Fagopyrum, Fragaria, Geranium, Glycine, Gossypium, Helianthus, Hordeum, Hemerocallis, Lactuca, Lens, Lolium, Lotus, Lycopersicon, Majorana, Manihot, Medicago, Nasturtium, Nicotiana, Oryza, Pelargonium, Persea, Petunia, Phaseolus, Pisum, Ranunculus, Raphanus, Ricinus, Saccharrum, Secale, Senecio, Setaria, Solanum, Spinacia, Trifolium, Triticum, Bromus, Cichorium, Hyoscyamus, Linum, Nemesia, Panicum, Onobrychis, Pennisetum, Salpiglossis, Sinapis, Trigonella, and Vigna.

Preferred plants that are to be transformed according to the methods of this invention are cereal crops, including maize, rye, barley, wheat, sorghum, oats, millet, rice, triticale, sunflower, alfalfa, rapeseed and soybean.

Synthetic DNA sequences can then be prepared which code for the appropriate sequence of amino acids, and this synthetic DNA sequence can be inserted into an appropriate plant expression cassette.

Likewise, numerous plant expression cassettes and vectors are well known in the art. By the term "expression cassette" is meant a complete set of control sequences including initiation, promoter and termination sequences which function in a plant cell when they flank a structural gene in the proper reading frame. Expression cassettes frequently and preferably contain an assortment of restriction sites suitable for cleavage and insertion of any desired structural gene. It is important that the cloned gene have a start codon in the correct reading frame for the structural sequence. In addition, the plant expression cassette preferably includes a strong constitutive promoter sequence at one end to cause the gene to be transcribed at a high frequency, and a poly-A recognition sequence at the other end for proper processing and transport of the messenger RNA. An example of such a preferred (empty) expression cassette into which the cDNA of the present invention can be inserted is the pPHI414 plasmid developed by Beach et al. of Pioneer Hi-Bred International, Inc., Johnston, Iowa, as disclosed in U.S. patent application Ser. No. 07/785,648, filed Oct. 31, 1991, the disclosures of which are hereby incorporated herein by reference. Highly preferred plant expression cassettes will be designed to include one or more selectable marker genes, such as kanamycin resistance or herbicide tolerance genes.

By the term "vector" herein is meant a DNA sequence which is able to replicate and express a foreign gene in a host cell. Typically, the vector has one or more endonuclease recognition sites which may be cut in a predictable fashion by use of the appropriate enzyme. Such vectors are preferably constructed to include additional structural gene sequences imparting antibiotic or herbicide resistance, which then serve as markers to identify and separate transformed cells. Preferred markers/selection agents include kanamycin, chlorosulfuron, phosphonothricin, hygromycin and methotrexate. A cell in which the foreign genetic material in a vector is functionally expressed has been "transformed" by the vector and is referred to as a "transformant."

A particularly preferred vector is a plasmid, by which is meant a circular double-stranded DNA molecule which is not a part of the chromosomes of the cell.

As mentioned above, both genomic and cDNA encoding the gene of interest may be used in this invention. The vector of interest may also be constructed partially from a cDNA clone and partially from a genomic clone. When the gene of interest has been isolated, genetic constructs are made which contain the necessary regulatory sequences to provide for efficient expression of the gene in the host cell. According to this invention, the genetic construct will contain (a) a first genetic sequence coding for the protein or trait of interest and (b) one or more regulatory sequences operably linked on either side of the structural gene of interest. Typically, the regulatory sequences will be selected from the group comprising of promoters and terminators. The regulatory sequences may be from autologous or heterologous sources.

Promoters that may be used in the genetic sequence include nos, ocs and CaMV promoters.

An efficient plant promoter that may be used is an overproducing plant promoter. Overproducing plant promoters that may be used in this invention include the promoter of the small sub-unit (ss) of the ribulose-1,5-biphosphate carboxylase from soybean (Berry-Lowe et al., *J. Molecular and App. Gen.*, 1:483–498 (1982)), and the promoter of the cholorophyll a-b binding protein. These two promoters are known to be light-induced, in eukaryotic plant cells (see, for example, *Genetic Engineering of Plants, An Agricultural Perspective*, A. Cashmore, Pelham, N.Y., 1983, pp. 29–38, G. Coruzzi et al., *J. Biol. Chem.*, 258:1399 (1983), and P. Dunsmuir, et al., *J. Molecular and App. Gen.*, 2:285 (1983)).

The expression cassette comprising the structural gene for the protein of this invention operably linked to the desired control sequences can be ligated into a suitable cloning vector. In general, plasmid or viral (bacteriophage) vectors containing replication and control sequences derived from species compatible with the host cell are used. The cloning vector will typically carry a replication origin, as well as specific genes that are capable of providing phenotypic selection markers in transformed host cells. Typically, genes conferring resistance to antibiotics or selected herbicides are used. After the genetic material is introduced into the target cells, successfully transformed cells and/or colonies of cells can be isolated by selection on the basis of these markers.

Typically, an intermediate host cell will be used in the practice of this invention to increase the copy number of the cloning vector. With an increased copy number, the vector containing the gene of interest can be isolated in significant quantities for introduction into the desired plant cells. Host cells that can be used in the practice of this invention include prokaryotes, including bacterial hosts such as *E. coli, S. typhimurium*, and *Serratia marcescens*. Eukaryotic hosts such as yeast or filamentous fungi may also be used in this invention. Since these hosts are also microorganisms, it will be essential to ensure that plant promoters which do not cause expression of the protein in bacteria are used in the vector.

The isolated cloning vector will then be introduced into the plant cell using any convenient technique, including electroporation (in protoplasts), retroviruses, bombardment, and microinjection into cells from monocotyledonous or dicotyledonous plants in cell or tissue culture to provide transformed plant cells containing as foreign DNA at least one copy of the DNA sequence of the plant expression cassette. Preferably, the monocotyledonous species will be selected from maize, sorghum, wheat or rice, and the dicotyledonous species will be selected from soybean, alfalfa, rapeseed, sunflower or tomato. Using known techniques, protoplasts can be regenerated and cell or tissue culture can be regenerated to form whole fertile plants which carry and express the gene for a protein according to this invention. Accordingly, a highly preferred embodiment of the present invention is a transformed maize plant, the cells of which contain as foreign DNA at least one copy of the DNA sequence of an expression cassette of this invention.

Finally, this invention provides methods of imparting resistance to diseases caused by microorganisms selected from *F. graminearum, Fusarium moniliforme, F. oxysporum, A. flavus, P. medicaginis, Alternaria longipes, Colletototrichum graminicola, Verticillium albo-atrum, Phytophthora megasperme* f. sp. *glycinea, Macrophomina phaseolina, Diasporthe phaseolorum caulivor, Sclerotinia sclerotiorum*, and *Sclerotinia trifoliorum* to plants of a susceptible taxon, comprising the steps of:

a) culturing cells or tissues from at least one plant from the taxon, b) introducing into the cells or tissue culture at least one copy of an expression cassette comprising a structural gene for one or more of the compounds of this invention, operably linked to plant regulatory sequences which cause the expression of the compound or compounds in the cells, and c) regenerating disease-resistant whole plants from the cell or tissue culture. Once whole plants have been obtained, they can be sexually or clonally reproduced in such manner that at least one copy of the sequence provided by the expression cassette is present in the cells of progeny of the reproduction.

Alternatively, once a single transformed plant has been obtained by the foregoing recombinant DNA method, conventional plant breeding methods can be used to transfer the structural gene for the compound of this invention and associated regulatory sequences via crossing and backcrossing. Such intermediate methods will comprise the further steps of a) sexually crossing the disease-resistant plant with a plant from the disease-susceptible taxon;

b) recovering reproductive material from the progeny of the cross; and c) growing disease-resistant plants from the reproductive material. Where desirable or necessary, the agronomic characteristics of the susceptible taxon can be substantially preserved by expanding this method to include the further steps of repetitively:

a) backcrossing the disease-resistant progeny with disease-susceptible plants from the susceptible taxon; and b) selecting for expression of antimicrobial activity (or an associated marker gene) among the progeny of the backcross, until the desired percentage of the characteristics of the susceptible taxon are present in the progeny along with the gene imparting antimicrobial activity.

By the term "taxon" herein is meant a unit of botanical classification of genus or lower. It thus includes genus, species, cultivars, varieties, variants, and other minor taxonomic groups which lack a consistent nomenclature.

It will also be appreciated by those of ordinary skill that the plant vectors provided herein can be incorporated into *Agrobacterium tumefaciens*, which can then be used to transfer the vector into susceptible plant cells, primarily from *dicotyledonous* species. Thus, this invention provides a method for imparting antimicrobial activity and disease resistance in *Agrobacterium tumefaciens*-susceptible *dicotyledonous* plants in which the expression cassette is introduced into the cells by infecting the cells with *Agrobacterium tumefaciens*, a plasmid of which has been modified to include a plant expression cassette of this invention.

Human and Veterinary Pharmaceutical Use

This invention also provides methods of treating and preventing infection by susceptible organisms in a human or lower animal host in need of such treatment, which method comprises administration to the human or lower animal host in need of such treatment a therapeutically effective amount of a polypeptide of this invention or a composition containing one or more of the polypeptides. The polypeptides of the present invention may be administered parenterally, by inhalation spray, rectally or topically in dosage unit formulations containing conventional nontoxic pharmaceutically acceptable carriers, adjuvants and vehicles as desired. The term parenteral as used herein includes subcutaneous, intravenous, intramuscular, intraarticular and intrathecal injection and infusion techniques. As with other polypeptides, the polypeptides of this invention are not known to be active orally.

Total daily dose of the compounds of this invention administered to a host in single or divided doses may be in amounts, for example, of from 1 to 2000 mg/kg body weight daily and more usually 50 to 500 mg/kg. Dosage unit compositions may contain such amounts or fractions or submultiples thereof as appropriate to make up the daily dose. It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

This invention also provides pharmaceutical compositions in unit dosage form, comprising an effective amount of a compound of this invention in combination with a conventional pharmaceutical carrier. As used herein, the term "pharmaceutical carrier" means a solid or liquid filler, diluent or encapsulating material. Some examples of the materials which can serve as pharmaceutical carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such peanut oil, cottonseed oil, safflower oil, sesame oil, olive oil, corn oil and soybean oil; polyols such as propylene glycol, glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution, ethyl alcohol and phosphate buffer solutions, as well as other non-toxic compatible substances used in pharmaceutical formulations. Wetting agents, emulsifiers and lubricants such as sodium lauryl sulfate and magnesium stearate, as well as coloring agents, release agents, coating agents, and perfuming agents and preservatives can also be present in the compositions, according to the desires of the formulator. The amount of active ingredient that may be combined with the carrier materials to produce a single dosage form will vary depending upon the host treated and the particular mode of administration.

By "therapeutically effective amount" herein is meant an amount of either polypeptide or combination thereof sufficient to provide antimicrobial activity so as to alleviate or prevent infection by susceptible organisms in the human or lower animal being treated at a reasonable benefit/risk ratio attendant with any medical treatment.

Antimicrobial Testing

The antifungal activity of compounds synthesized in accord with this invention was measured using art-recognized methods, as described in Duvick et al., *J.Biol.Chem.* 26:18814–18820 (1992). Results are as follows:

TABLE 1

Antifungal Activity of Synthetic Peptides

| Peptide* | A. flavus | | F. graminearum | | F. moniliforme | |
|---|---|---|---|---|---|---|
| | MIC | MCIC | MIC | MCIC | MIC | MCIC |
| 1 | NA | NA | 17 | >40 | 17 | >40 |
| 2 | 40 | >80 | 14 | 19 | 14 | 39 |
| 3 | NA | NA | 13 | 26 | 13 | 26 |
| 4 | NA | NA | 13 | 51 | 17 | 136 |
| 6 | 80 | >80 | 10 | 20 | 15 | 40 |
| 7 | 40 | >80 | 10 | 40 | 10 | 40 |
| 9 | 15 | 80 | 10 | 20 | 10 | 15 |
| 10 | 80 | >80 | 10 | 20 | 7.5 | 10 |
| Cecropin A | 80 | >80 | 60 | >80 | 80 | >80 |
| Mastoparan | 20 | 40 | 5 | 10 | 2.5 | 10 |
| 16 | 30 | >80 | 10 | 20 | 5 | 40 |
| 17 | 40 | >80 | 7.5 | 15 | 20 | 20 |
| 18 | 40 | >80 | 10 | 20 | 10 | 20 |
| 19 | 5 | 80 | 3.74 | 10 | 2.5 | 10 |
| 20 | 12.5 | >80 | 3.75 | 10 | 5 | 10 |
| 21 | 30 | >80 | 40 | >80 | 15 | >80 |
| 22 | 15 | >80 | 20 | 40 | 10 | 40 |

*Peptides of this invention are identified by their SEQUENCE I.D. Nos.

MIC is the minimum inhibitory concentration, the concentration in µg/ml achieving a score of 1 or greater (25% growth inhibition). MCIC is the Minimum Complete Inhibitory Concentration, the concentration in µg/ml achieving a score of 3 or greater (≧80% growth inhibition). The ">" symbol indicates that the MIC or MGIC was higher than the highest tested concentration.

Proteins of SEQUENCE I.D. Nos. 19, 20 and 22 also showed significant activity against other gram negative and gram positive organisms. The protein having SEQUENCE I.D. No. 19 had MICs/MCICs against *E. coli, A. tumefaciens* and *C. nebraskense* of 6.25/25, 6.25/>100 and 3.13/12.5 µg per ml, respectively, and the protein having SEQUENCE I.D. No. 20 had MICs/MCICs against *E. coli, A. tumefaciens* and *C. nebraskense* of 3.13/25, 3.13/50 and 3.13/12.5 µg per ml, respectively. The protein having SEQUENCE I.D. No. 22 had MICs/MCICs against *E. coli* and *C. nebraskense* of 3.13/>100 and 12.5/50 µg per ml, respectively

TABLE 2

Antimicrobial Activity Expressed as % Inhibition of Growth

| Peptide | Concentration (µg/ml) | | | | | |
|---|---|---|---|---|---|---|
| | 100 | 50 | 25 | 12.5 | 6.25 | 3.00 |
| *E. coli* | | | | | | |
| 1 | 15 | 4 | 0 | 0 | 0 | 0 |
| 2 | 44 | 38 | 35 | 30 | 26 | 8 |
| 3 | | 0 | 0 | 0 | 0 | 0 |
| 4 | | 0 | 0 | 0 | 0 | 0 |
| 5 | | 0 | 0 | 0 | 0 | 0 |
| 10 | | 0 | 0 | 0 | 0 | 0 |
| *P. syringae* | | | | | | |
| 1 | 72 | 27 | 10 | 5 | 2 | 0 |
| 2 | 95 | 92 | 91 | 90 | 90 | 83 |
| 3 | | 52 | 48 | 30 | 11 | 0 |
| 4 | | 32 | 27 | 14 | 3 | 0 |
| 5 | 100 | 100 | 56 | 30 | 20 | 12 |
| 10 | | 48 | 27 | 19 | 0 | 0 |

TABLE 2-continued

Antimicrobial Activity Expressed as % Inhibition of Growth

| Peptide | Concentration (µg/ml) | | | | | |
|---|---|---|---|---|---|---|
| | 100 | 50 | 25 | 12.5 | 6.25 | 3.00 |
| *E. stewartii* | | | | | | |
| 1 | — | — | — | — | — | — |
| 2 | — | — | — | — | — | — |
| 3 | | 100 | 80 | 49 | 0 | 0 |
| 4 | | 100 | 100 | 57 | 55 | 54 |
| 5 | | 100 | 100 | 62 | 47 | 42 |
| 10 | | 0 | 0 | 0 | 0 | 0 |
| *B. pumilus* | | | | | | |
| 1 | 77 | 25 | 19 | 9 | 7 | 0 |
| 2 | 87 | 69 | 22 | 0 | 0 | 0 |
| 3 | — | — | — | — | — | — |
| 4 | — | — | — | — | — | — |
| 5 | — | — | — | — | — | — |
| 10 | — | — | — | — | — | — |

What is claimed is:

1. A protein having the sequence of any of SEQUENCE I.D. No. 1, SEQUENCE I.D. No. 2, SEQUENCE I.D. No. 3, SEQUENCE I.D. No. 4, SEQUENCE I.D. No. 5, SEQUENCE I.D. No. 6, SEQUENCE I.D. No. 7, SEQUENCE I.D. No. 8, SEQUENCE I.D. No. 9, SEQUENCE I.D. No. 10, SEQUENCE I.D. No. 11, SEQUENCE I.D. No. 12, SEQUENCE I.D. No. 17, SEQUENCE I.D. No. 18, SEQUENCE I.D. No. 19, SEQUENCE I.D. No. 20, SEQUENCE I.D. No. 21, or SEQUENCE I.D. No. 22.

2. A peptide of from 15 to 30 amino acids comprising the sequence of SEQUENCE I.D. No. 16 and having a hydrophobicity of from −0.34 to −0.50 and a hydrophobic moment of from 0.60 to 0.84.

* * * * *

UNITED STATES PATENT AND TRADEMARK OFFICE
CERTIFICATE OF CORRECTION

PATENT NO. : 5,717,061
DATED : February 10, 1998
INVENTOR(S) : A. Gururaj Rao and Lingxiu Zhong It is certified that error appears in the above-identified patent and that said Letters Patent is hereby corrected as shown below:

Title page, item [54] and Col. 1, line 1, should read :

SYNTHETIC ANTIMICROBIAL PEPTIDES

Signed and Sealed this

Fifth Day of May, 1998

Attest:

BRUCE LEHMAN

*Attesting Officer*            *Commissioner of Patents and Trademarks*

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 32 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:1:

```
Lys Lys Ile Glu Lys Ala Ile Lys His Ile Pro Lys Lys Ile Lys Ala
1               5                   10                  15
Gly Pro Gly Val Thr Ile Gly Ile Ala His Ala Lys Ser Gln Leu Trp
            20                  25                  30
```

( 2 ) INFORMATION FOR SEQ ID NO:2:

( i ) SEQUENCE CHARACTERISTICS:
        ( A ) LENGTH: 31 amino acids (B) TYPE: amino acid
(C) STRANDEDNESS:
(D) TOPOLOGY: linear (ii) MOLECULE TYPE: protein (xi) SEQUENCE DESCRIPTION: SEQ ID NO:2:

Lys Leu Lys Lys Ala Leu Arg Ala Leu Ala Arg His Trp Lys Ala Gly
1               5                   10                  15

Pro Gly Val Thr Ile Gly Ile Ala His Ala Lys Ser Gln Leu Trp
            20                  25                  30

(2) INFORMATION FOR SEQ ID NO:3:

(i) SEQUENCE CHARACTERISTICS:
    (A) LENGTH: 40 amino acids
    (B) TYPE: amino acid
    (C) STRANDEDNESS:
    (D) TOPOLOGY: linear (ii) MOLECULE TYPE: protein (xi) SEQUENCE DESCRIPTION: SEQ ID NO:3:

Gln Arg Ala Val Arg Arg Ile Tyr Arg Ala Ile Arg His Ile Pro Arg
1               5                   10                  15

Arg Ile Arg Ile Arg Ala Leu Ala Gly Pro Gly Val Thr Ile Gly Ile
            20                  25                  30

Ala His Ala Lys Ser Gln Leu Trp
        35                  40

(2) INFORMATION FOR SEQ ID NO:4:

(i) SEQUENCE CHARACTERISTICS:
    (A) LENGTH: 40 amino acids
    (B) TYPE: amino acid
    (C) STRANDEDNESS:
    (D) TOPOLOGY: linear (ii) MOLECULE TYPE: protein (xi) SEQUENCE DESCRIPTION: SEQ ID NO:4:

Gln Arg Ala Val Lys Lys Ile Glu Lys Ala Ile Lys His Ile Pro Lys
1               5                   10                  15

Lys Ile Lys Ile Arg Ala Leu Ala Gly Pro Gly Val Thr Ile Gly Ile
            20                  25                  30

Ala His Ala Lys Ser Gln Leu Trp
        35                  40

(2) INFORMATION FOR SEQ ID NO:5:

(i) SEQUENCE CHARACTERISTICS:
    (A) LENGTH: 40 amino acids
    (B) TYPE: amino acid
    (C) STRANDEDNESS:
    (D) TOPOLOGY: linear (ii) MOLECULE TYPE: protein (xi) SEQUENCE DESCRIPTION: SEQ ID NO:5:

Ile Gln Arg Val Ala Gln Lys Leu Lys Lys Ala Leu Arg Ala Leu Ala
1               5                   10                  15

Arg His Trp Lys Arg Ala Leu Ala Gly Pro Gly Val Thr Ile Gly Ile
            20                  25                  30

Ala His Ala Lys Ser Gln Leu Trp
        35                  40

( 2 ) INFORMATION FOR SEQ ID NO:6:

( i ) SEQUENCE CHARACTERISTICS:
        ( A ) LENGTH: 43 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:6:

```
Ile Arg Ala Leu Gln Arg Ala Val Arg His Pro Arg Ala Ile Arg Arg
 1               5                  10                  15

Ile Tyr Arg Gly Trp Lys Lys Ala Ile Arg Ala Gly Pro Gly Val Thr
            20                  25                  30

Ile Gly Ile Ala His Ala Lys Ser Gln Leu Trp
        35                  40
```

( 2 ) INFORMATION FOR SEQ ID NO:7:

( i ) SEQUENCE CHARACTERISTICS:
        ( A ) LENGTH: 38 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:7:

```
Lys Leu Ile Arg Lys Leu Ile Arg Trp Leu Arg Arg Lys Ile Arg Ala
 1               5                  10                  15

Leu Gln Arg Ala Val Ala Gly Pro Gly Val Thr Ile Gly Ile Ala His
            20                  25                  30

Ala Lys Ser Gln Leu Trp
        35
```

( 2 ) INFORMATION FOR SEQ ID NO:8:

( i ) SEQUENCE CHARACTERISTICS:
        ( A ) LENGTH: 41 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:8:

```
Gln Arg Ala Val Gly Trp Leu Arg Arg Ile Gly Arg Arg Ile Glu Arg
 1               5                  10                  15

Val Gly Gln His Leu Arg Ala Leu Ala Gly Pro Gly Val Thr Ile Gly
            20                  25                  30

Ile Ala His Ala Lys Ser Gln Leu Trp
        35                  40
```

( 2 ) INFORMATION FOR SEQ ID NO:9:

( i ) SEQUENCE CHARACTERISTICS:
        ( A ) LENGTH: 31 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:9:

```
Arg Arg Ile Tyr Arg Ala Ile Arg His Ile Pro Arg Arg Ile Arg Gly
```

```
                   1                   5                              10                             15
              Trp  Leu  Arg  Arg  Ile  Gly  Arg  Arg  Ile  Glu  Arg  Val  Gly  Gln  His
                             20                       25                       30
```

(2) INFORMATION FOR SEQ ID NO:10:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:10:

```
    Lys  Lys  Ile  Glu  Lys  Ala  Ile  Lys  His  Ile  Pro  Lys  Lys  Ile  Lys  Leu
    1                   5                            10                           15
    Lys  Lys  Ala  Leu  Arg  Ala  Leu  Ala  Arg  His  Trp  Lys
                   20                       25
```

(2) INFORMATION FOR SEQ ID NO:11:

(i) SEQUENCE CHARACTERISTICS:
        (A) LENGTH: 30 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:11:

```
    Gly  Trp  Leu  Arg  Arg  Ile  Gly  Arg  Arg  Ile  Glu  Arg  Val  Gly  Gln  His
    1                   5                            10                           15
    Lys  Leu  Lys  Lys  Ala  Leu  Arg  Ala  Leu  Ala  Arg  His  Trp  Lys
                   20                       25                       30
```

(2) INFORMATION FOR SEQ ID NO:12:

(i) SEQUENCE CHARACTERISTICS:
        (A) LENGTH: 30 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:12:

```
    Lys  Leu  Lys  Lys  Ala  Leu  Arg  Ala  Leu  Ala  Arg  His  Trp  Lys  Gly  Trp
    1                   5                            10                           15
    Leu  Arg  Arg  Ile  Gly  Arg  Arg  Ile  Glu  Arg  Val  Gly  Gln  His
                   20                       25                       30
```

(2) INFORMATION FOR SEQ ID NO:13:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:13:

```
    Ala  Ile  Ala  Lys  Phe  Ala  Lys  Lys  Ala  Leu  Lys  Ser  Met  Leu  Ala  Leu
    1                   5                            10                           15
    Met  Gly  Glu  Ala  Val  Gln  Thr
                   20
```

( 2 ) INFORMATION FOR SEQ ID NO:14:

( i ) SEQUENCE CHARACTERISTICS:
        ( A ) LENGTH: 23 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:14:

```
Ala  Ile  Ala  Ile  Phe  Lys  Arg  Ile  Ala  Lys  Ile  Asn  Phe  Lys  Ala  Leu
1                   5                        10                       15

Met  Gly  Glu  Ala  Val  Gln  Thr
                20
```

( 2 ) INFORMATION FOR SEQ ID NO:15:

( i ) SEQUENCE CHARACTERISTICS:
        ( A ) LENGTH: 23 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:15:

```
Ala  Ile  Ala  Asn  Phe  Glu  Arg  Leu  Met  Lys  Lys  Leu  Ile  Trp  Ala  Leu
1                   5                        10                       15

Met  Gly  Glu  Ala  Val  Gln  Thr
                20
```

( 2 ) INFORMATION FOR SEQ ID NO:16:

( i ) SEQUENCE CHARACTERISTICS:
        ( A ) LENGTH: 14 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:16:

```
Lys  Leu  Lys  Lys  Ala  Leu  Arg  Ala  Leu  Ala  Arg  His  Trp  Lys
1                   5                        10
```

( 2 ) INFORMATION FOR SEQ ID NO:17:

( i ) SEQUENCE CHARACTERISTICS:
        ( A ) LENGTH: 23 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:17:

```
Ile  Gln  Arg  Val  Ala  Gln  Lys  Leu  Lys  Lys  Ala  Leu  Arg  Ala  Leu  Ala
1                   5                        10                       15

Arg  His  Trp  Lys  Arg  Ala  Leu
                20
```

( 2 ) INFORMATION FOR SEQ ID NO:18:

( i ) SEQUENCE CHARACTERISTICS:
        ( A ) LENGTH: 26 amino acids
        ( B ) TYPE: amino acid (C) STRANDEDNESS:
(D) TOPOLOGY: linear (i i) MOLECULE TYPE: protein (x i) SEQUENCE DESCRIPTION: SEQ ID NO:18:

```
Ile Arg Ala Leu Gln Arg Ala Val Arg His Pro Arg Ala Ile Arg Arg
 1               5                  10                  15
Ile Tyr Arg Gly Trp Lys Lys Ala Ile Arg
            20                  25
```

(2) INFORMATION FOR SEQ ID NO:19:

(i) SEQUENCE CHARACTERISTICS:
(A) LENGTH: 14 amino acids
(B) TYPE: amino acid
(C) STRANDEDNESS:
(D) TOPOLOGY: linear (i i) MOLECULE TYPE: protein (x i) SEQUENCE DESCRIPTION: SEQ ID NO:19:

```
Lys Trp Lys Lys Ala Leu Arg Ala Leu Ala Arg His Leu Lys
 1               5                  10
```

(2) INFORMATION FOR SEQ ID NO:20:

(i) SEQUENCE CHARACTERISTICS:
(A) LENGTH: 14 amino acids
(B) TYPE: amino acid
(C) STRANDEDNESS:
(D) TOPOLOGY: linear (i i) MOLECULE TYPE: protein (x i) SEQUENCE DESCRIPTION: SEQ ID NO:20:

```
Lys Leu Lys Lys Ala Leu Arg Trp Leu Ala Arg His Ala Lys
 1               5                  10
```

(2) INFORMATION FOR SEQ ID NO:21:

(i) SEQUENCE CHARACTERISTICS:
(A) LENGTH: 14 amino acids
(B) TYPE: amino acid
(C) STRANDEDNESS:
(D) TOPOLOGY: linear (i i) MOLECULE TYPE: protein (x i) SEQUENCE DESCRIPTION: SEQ ID NO:21:

```
Gly Ala Tyr Arg Ala Ile Arg His Ile Pro Arg Arg Ile Arg
 1               5                  10
```

(2) INFORMATION FOR SEQ ID NO:22:

(i) SEQUENCE CHARACTERISTICS:
(A) LENGTH: 15 amino acids
(B) TYPE: amino acid
(C) STRANDEDNESS:
(D) TOPOLOGY: linear (i i) MOLECULE TYPE: protein (x i) SEQUENCE DESCRIPTION: SEQ ID NO:22:

```
Arg Arg Ile Tyr Arg Ala Ile Arg His Ile Pro Arg Arg Ile Arg
 1               5                  10                  15
```